United States Patent
Lou et al.

(10) Patent No.: US 10,420,526 B2
(45) Date of Patent: Sep. 24, 2019

(54) OPTIMIZING CT SCANNING PARAMETER

(71) Applicant: Shenyang Neusoft Medical Systems Co., Ltd., Liaoning (CN)

(72) Inventors: Shanshan Lou, Liaoning (CN); Dan Lv, Liaoning (CN); Ling Pang, Liaoning (CN); Changkun Liu, Liaoning (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 395 days.

(21) Appl. No.: 14/986,556

(22) Filed: Dec. 31, 2015

(65) Prior Publication Data
US 2016/0183905 A1 Jun. 30, 2016

(30) Foreign Application Priority Data

Dec. 31, 2014 (CN) .......................... 2014 1 0850617
Dec. 9, 2015 (CN) .......................... 2015 1 0907759

(51) Int. Cl.
*A61B 6/00* (2006.01)
*G06T 7/00* (2017.01)
(Continued)

(52) U.S. Cl.
CPC .............. *A61B 6/583* (2013.01); *A61B 6/542* (2013.01); *A61B 6/545* (2013.01); *A61B 6/582* (2013.01);
(Continued)

(58) Field of Classification Search
CPC .. A61B 6/00; A61B 6/03; A61B 6/032; A61B 6/52; A61B 6/5258; A61B 6/5894;
(Continued)

(56) References Cited

U.S. PATENT DOCUMENTS

2005/0058250 A1* 3/2005 Popescu ................. A61B 6/032
378/109
2005/0129170 A1* 6/2005 Watson ................. G01T 1/2985
378/5
(Continued)

FOREIGN PATENT DOCUMENTS

CN 1593342 A 3/2005
CN 102576387 A 7/2012
(Continued)

OTHER PUBLICATIONS

CN Third Office Action dated Mar. 12, 2019 in the corresponding CN application (application No. 2915109611s9.2).

*Primary Examiner* — Anastasia Midkiff
(74) *Attorney, Agent, or Firm* — Kilpatrick Townsend & Stockton LLP

(57) ABSTRACT

A method for optimizing CT scanning parameter is disclosed. A target group may be generated from a plurality of reference information samples. Each of the reference information samples may include subject information, information indicating a scanning protocol, one or more scanning parameter values and information indicating reconstructed image quality; the target group can consist of one or more reference information samples with the same subject information and the same scanning protocol. A scanning parameter optimization may be performed according to reconstructed image qualities and scanning parameter values of reference information samples in the target group, so as to acquire a target scanning parameter value of the target group. And according to the target scanning parameter value, a reference X-ray irradiation dose corresponding to the scanning protocol and the subject information of the target group may be determined.

10 Claims, 6 Drawing Sheets

(51) Int. Cl.
*G01T 7/00* (2006.01)
*A61B 6/03* (2006.01)
*G01T 1/00* (2006.01)
*G09B 23/28* (2006.01)

(52) U.S. Cl.
CPC .......... G01T 7/005 (2013.01); G06T 7/0014 (2013.01); *A61B 6/032* (2013.01); *A61B 6/52* (2013.01); *A61B 6/5258* (2013.01); *A61B 6/58* (2013.01); *A61B 2560/0223* (2013.01); *G01T 1/00* (2013.01); *G09B 23/286* (2013.01)

(58) Field of Classification Search
CPC ........... A61B 6/542; A61B 6/545; A61B 6/58; A61B 6/582; A61B 6/583; A61B 2560/00; A61B 2560/02; A61B 2560/0223; A61B 2560/0233; A61B 2560/0238; G01T 7/00; G01T 7/005; G06T 7/00; G06T 7/0012; G06T 7/0014; G06T 2207/00; G06T 2207/10; G06T 2207/10072; G06T 2207/10081; G06T 2207/20172; G06T 2207/30; G06T 2207/30004; G06T 2210/00; G06T 2210/41; G06T 2211/00; G06T 2211/40; G09B 23/00; G09B 23/28; G09B 23/286; G09B 23/30

See application file for complete search history.

(56) References Cited

U.S. PATENT DOCUMENTS

| | | | |
|---|---|---|---|
| 2005/0129179 A1* | 6/2005 | McGovern | G03C 3/003 378/169 |
| 2006/0262896 A1 | 11/2006 | Nishide et al. | |
| 2007/0258559 A1* | 11/2007 | Hur | A61B 6/481 378/16 |
| 2012/0018645 A1 | 1/2012 | Vija | |
| 2013/0105699 A1 | 5/2013 | Asma et al. | |
| 2014/0270053 A1* | 9/2014 | Larson | A61B 6/032 378/4 |
| 2015/0085984 A1* | 3/2015 | Li | A61B 6/542 378/93 |
| 2016/0063686 A1* | 3/2016 | Lou | G06T 5/002 382/131 |

FOREIGN PATENT DOCUMENTS

| | | |
|---|---|---|
| CN | 103247061 A | 8/2013 |
| CN | 103901379 A | 7/2014 |
| CN | 103987321 A | 8/2014 |
| CN | 104039262 A | 9/2014 |
| JP | 2007325641 A | 12/2007 |
| WO | 2011048515 A2 | 4/2011 |
| WO | 2011154853 A1 | 12/2011 |

* cited by examiner (Abstract Figure)

OPTIMIZING CT SCANNING PARAMETER

CROSS-REFERENCES TO RELATED APPLICATION

This application is a provisional application and claims the benefit and priority of Chinese Patent Application No. 201410850617.2, filed on Dec. 31, 2014 titled "OPTIMIZING CT SCANNING PARAMETERS", and the benefit and priority of Chinese Patent Application No. 20150907759.2 filed on Dec. 9, 2015 titled 10 "OPTIMIZING CT SCANNING PARAMETERS", both of which are herein incorporated by reference in its entirety for all purposes

BACKGROUND

The present disclosure relates to the technical field of medical equipment.

Usually, by scanning a specific region of a subject such as a patient with a CT scanner system, a reconstructed image may be acquired, and further, different scanning parameter values may lead to reconstructed images with different qualities. Generally, a reconstructed image of which image quality is very low may not be suitable for clinical diagnosis, and oppositely, a reconstructed image of which image quality is very high may indicate an excessive X-ray irradiation which may be harmful to the subject.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, MM, digital X-ray machine, Ultrasound, PET (Positron Emission Tomography), Linear Accelerator, and Biochemistry Analyser. Currently, NMS' products are exported to over 60 countries and regions around the globe, serving more than 5,000 renowned customers. NMS's latest successful developments, such as 128 Multi-Slice CT Scanner System, Superconducting MM, Linear Accelerator, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

BRIEF DESCRIPTION OF DRAWINGS

Features of the present disclosure are illustrated by way of examples and not limited in the following figure(s), in which like numerals indicate like elements, in which.

DETAILED DESCRIPTION

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

Figure 1:
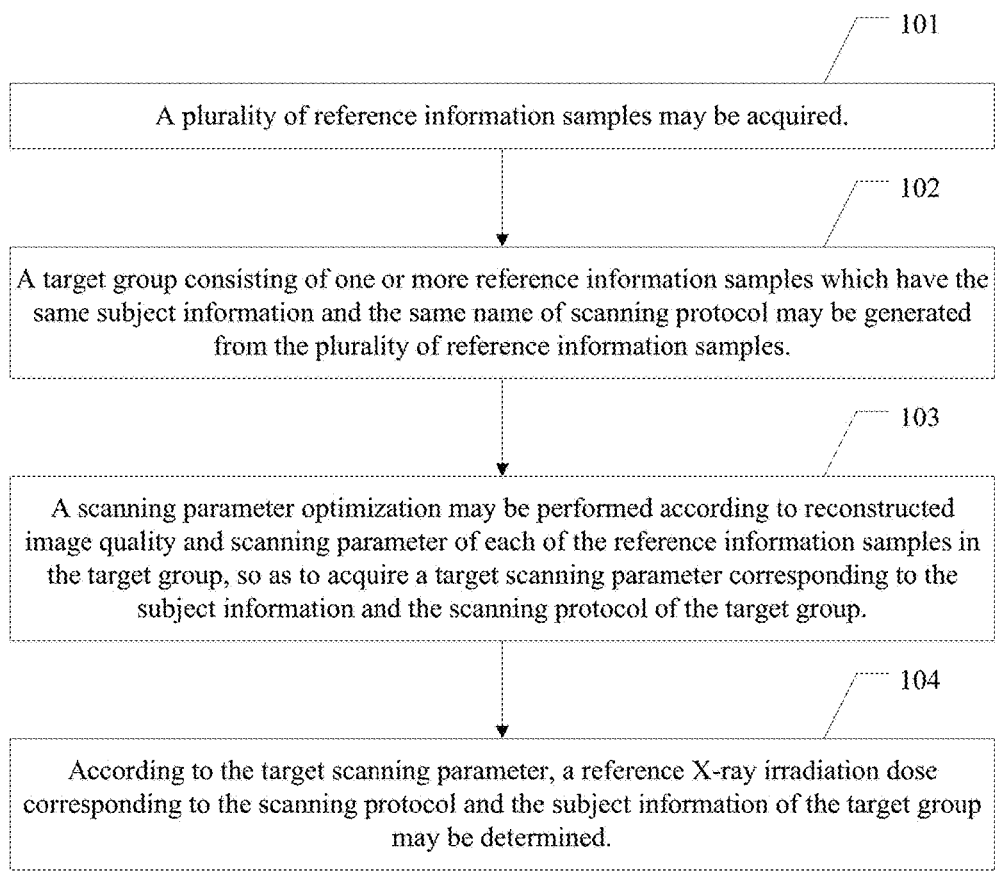
FIG. 1 is a flowchart illustrating a method for optimizing CT scanning parameter according to an example of the present disclosure.

The present disclosure provides a method for optimizing CT scanning parameter, which may reduce X-ray irradiation dose applied on a subject while ensure requirements of clinical diagnosis are still satisfied. FIG. 1 illustrates a method for optimizing CT scanning parameter according to an example of the present disclosure, and the method may include blocks 101-104.

At block 101, a plurality of reference information samples may be acquired, wherein, each of the reference information samples may include subject information, information indicating a scanning protocol, one or more scanning parameter values and information indicating reconstructed image quality obtained accordingly.

At block 102, a target group consisting of one or more reference information samples with the same subject information and the same scanning protocol may be generated from the plurality of reference information samples.

At block 103, a scanning parameter optimization may be performed according to reconstructed image qualities and scanning parameter values of reference information samples in the target group, so as to acquire a target scanning parameter value corresponding to the subject information and the scanning protocol of the target group.

At block 104, according to the target scanning parameter value, a reference X-ray irradiation dose corresponding to the scanning protocol and the subject information of the target group may be determined.

In the present example, reference information samples may be grouped according to subject information and scanning protocol, for example, two or more reference information samples with the same subject information and the same scanning protocol may be grouped as a target group. Then, by adjusting a scanning parameter value according to reconstructed image qualities in the target group, an optimal scanning parameter value may be acquired as a target scanning parameter value. Further, a reference X-ray irradiation dose corresponding to the subject information and the scanning protocol of the target group may be calculated according to the target scanning parameter value. And thus, a to-be-scanned region of a subject may be scanned with an X-ray irradiation dose corresponding to the optimal scanning parameter value with respect to the subject information and the scanned region, which may reduce the X-ray irradiation dose applied on the subject and obtain a reconstructed image satisfying the requirement for clinical diagnosis at the same time.

Figure 2:
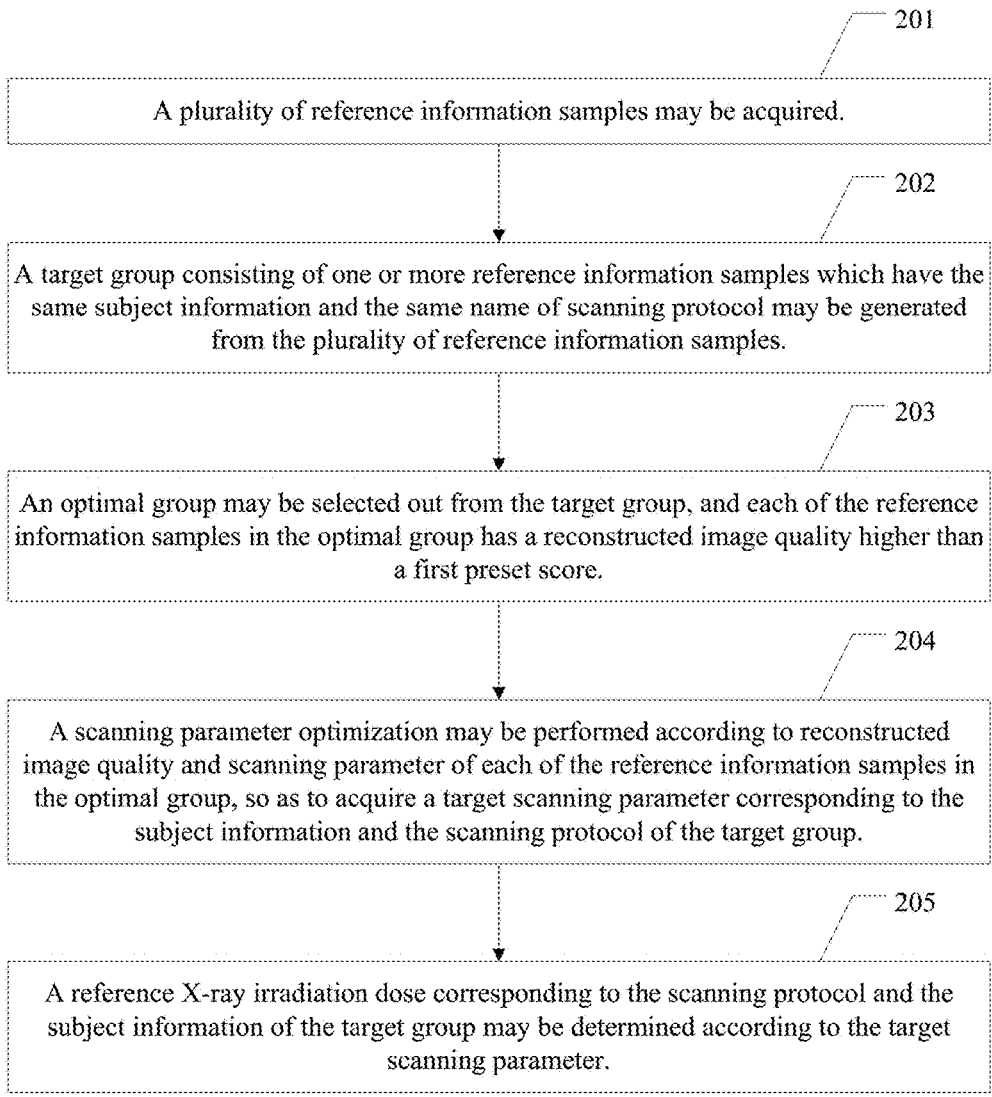
FIG. 2 is a flowchart illustrating a method for optimizing CT scanning parameter according to another example of the present disclosure.

FIG. 2 illustrates a method for optimizing CT scanning parameter according to another example of the present disclosure, and the method may include blocks 201-205.

At block 201, a plurality of reference information samples may be acquired, wherein, each of the reference information samples may include subject information, information indicating a scanning protocol, one or more scanning parameter values and information indicating reconstructed image quality obtained accordingly.

It should be noted that, the term "scanning protocol" may indicate a region which is scanned or to be scanned. And a name of scanning protocol may be recorded in a reference information sample to represent a scanning protocol.

The subject information may include one or more selected from the following: body size, gender, age and body mass index.

The scanning parameters may include one or more of the following: tube current, tube voltage, scanning time, scanning slice thickness, pitch and scanning volume. Usually, the X-ray irradiation dose may increase as the tube voltage, tube current, scanning time and scanning volume increasing, and decrease as the pitch increasing. For example, when the tube voltage increases from 120 kv to 140 kv, the X-ray irradiation dose may increase by 30%-40% in a case that other scanning parameters remain unchanged. Lowering the tube voltage may lower the X-ray irradiation dose, but may also lower the reconstructed image quality. As another example, the X-ray irradiation dose may be linear correlated with a product of the tube current and the time (milli-ampere second, mAs) in a case that other scanning parameters remain unchanged. Lowering the tube current may lower the X-ray irradiation dose, but may also increase noise in the reconstructed image. As still another example, the pitch is inversely proportional to the X-ray irradiation dose. Increasing the pitch may decrease the X-ray irradiation dose, but may also decrease a spatial resolution on Z-axis and negatively influence the reconstructed image quality.

The reconstructed image quality may include a score indicating an evaluation on quality of the reconstructed image, such as a score indicating overall quality, a score indicating noise level, a score indicating artefact level, a score indicating windmill artefact level or a score indicating cone-beam artefact level. According to an example, the reconstructed image quality may be a score given out by a doctor for the reconstructed image. Wherein, the score may be given out according to a scoring system of 5 point, 10 point, or any other point. The evaluation may be based on overall quality, noise level, artefact level or any other quality related factors of the reconstructed image. For example, in a 5 point scoring system, a 5 point score may represent excellent quality and indicate that the reconstructed image is sufficiently clear, a 4 point score may represent generally good quality and indicate that the reconstructed image is clear, a 3 point score may represent medium quality and indicate that the reconstructed image has a few of artefact and noise but can be used for disease diagnosis, a 2 point score may represent bad quality and indicate that the reconstructed image has obvious artefact and noise, and a 1 point score may represent seriously bad quality and indicate that the reconstructed image is not suitable for disease diagnosis.

According to an example, the subject information may be an X-ray attenuation diameter of equivalent water phantom and, since an X-ray beam may be attenuated at different degrees after passing through subjects of different sizes, the X-ray attenuation diameter of equivalent water phantom may be calculated according to pilot film data or projection data as follows.

Figure 7:
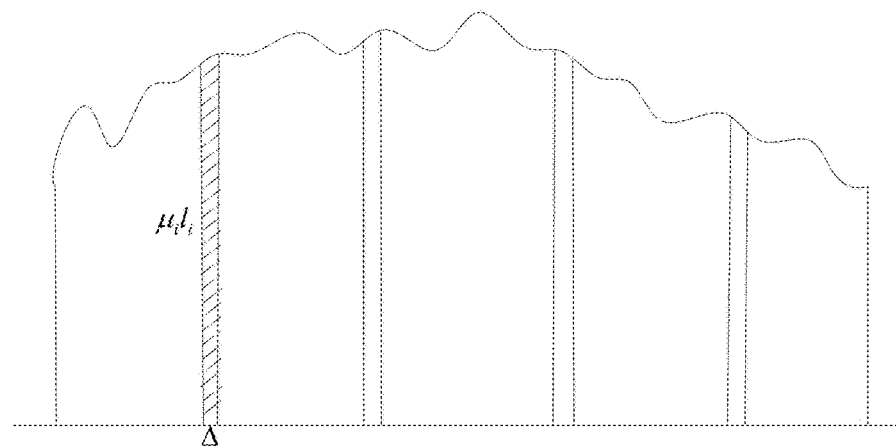
FIG. 7 schematically illustrates X-ray projection data of a subject which is acquired in a CT scanning and to be used for calculating an attenuation diameter of equivalent water phantom.

Firstly, pilot film data of a slice corresponding to a reference information sample or projection data of a field view image in the reference information sample may be converted into an equivalent attenuation domain. For example, FIG. 7 illustrates data in the equivalent attenuation domain which is obtained by converting pilot film data of the slice or projection data of the field view image into the equivalent attenuation domain. Wherein, the pilot film data and/or the projection data may be acquired from a CT scanning or a related database.

Next, an equivalent attenuation area may be calculated from the data in the equivalent attenuation domain. As illustrated in FIG. 7, the equivalent attenuation area may be viewed as sum of areas of a plurality of trapezoids, and the equivalent attenuation area S may be calculated as follows:

$$S = \sum_{i=0}^{N-1} (\mu_i l_i + \mu_{i+1} l_{i+1}) * \Delta / 2; \quad (1)$$

wherein, N represents a number of trapezoids in the equivalent attenuation domain and may correspond to a number of detecting channels in a CT scanner system;

$\mu_i$ represents an average attenuation coefficient corresponding to the $i^{th}$ detecting channel, $l_i$ represents length of attenuation path corresponding to the $i^{th}$ detecting channel, $\Delta$ represents an integration step length based on a center of an object and may correspond to a distance between centers of two adjacent detecting units.

Then, an attenuation diameter of equivalent water phantom may be calculated according to the equivalent attenuation area. For example, the attenuation diameter $D_{scan}$ of equivalent water phantom may be calculated as follows:

$$D_{scan} = 2 * \text{sqrt}(\text{mean}(S)/\pi)/\mu_{water} \quad (2);$$

wherein, $\mu_{water}$ represents an attenuation coefficient of water, and $\pi$ represents a circumference ratio and may also be referred as Pi.

Finally, the attenuation diameter of equivalent water phantom may be taken as a kind of subject information of the reference information sample. In this way, subjects having the same attenuation diameter of equivalent water phantom may be viewed as of the same body size.

According to another example, the subject information may be an equivalent diameter, and the equivalent diameter may be calculated according to a reconstructed image as follows.

Figure 8:
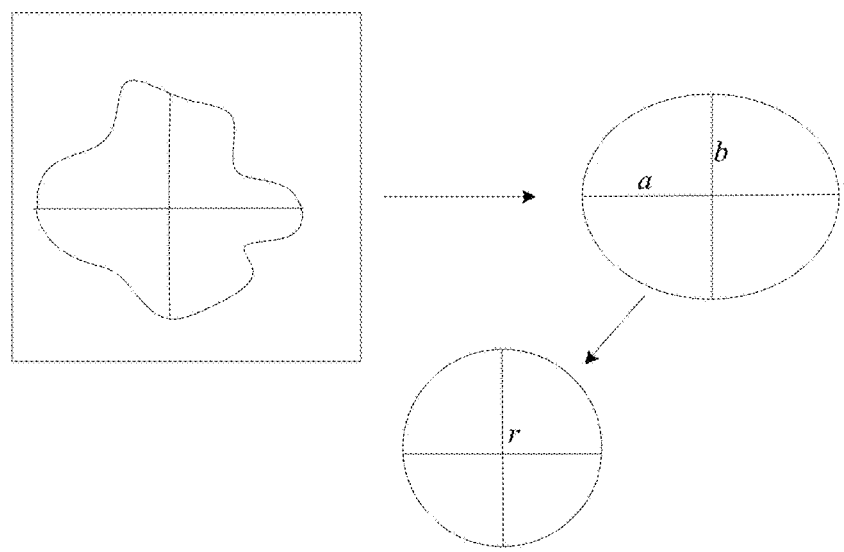
FIG. 8 schematically illustrates how an equivalent diameter of a subject is calculated based on a reconstructed image.
Figure 9:
FIG. 9 schematically illustrates an example equivalent water phantom.

Firstly, the major axis and the minor axis of a reconstructed image corresponding to a reference information sample may be determined, such as illustrated in the upper left part of FIG. 8.

Subsequently, an equivalent ellipse may be simulated according to the major axis and the minor axis, such as illustrated in the upper right part of FIG. 8.

Then, the equivalent ellipse may be converted into an equivalent circular of the same area, such as illustrated in the middle lower part of FIG. 8, and the diameter of the equivalent circular may be calculated as the equivalent diameter. For example, the diameter $D_{scan}$ of the equivalent circular may be calculated as follows:

$$D_{scan}=2*\sqrt{a*b} \quad (3);$$

wherein, 2a represents the major axis of the equivalent ellipse, 2b represents the minor axis of the equivalent ellipse.

Finally, the equivalent diameter may be taken as a kind of subject information. And thus, subjects having the same equivalent diameter may be viewed as of the same body size.

Besides the above mentioned examples, a skilled person in the art would understand that, any other ways may be adopted to determine the subject information.

At block 202, a target group consisting of one or more reference information samples with the same subject information and the same scanning protocol may be generated from the plurality of reference information samples.

For example, as illustrated in following Table 1, the reference information samples having the same scanning protocol "ProtocalA" and the same subject information "equivalent diameter of 400 mm" may be grouped as one target group.

TABLE 1

| Subject information (Equivalent diameter) | Scanning Protocol | Tube current | Tube voltage | Pitch | Reconstructed image quality (Overall quality score) |
|---|---|---|---|---|---|
| 400 mm | ProtocalA | 30 mA | 20 kv | .0 | 3 |
| 400 mm | ProtocalA | 50 mA | 20 kv | .7 | 4 |
| 400 mm | ProtocalA | 15 mA | 20 kv | .7 | 3 |
| 400 mm | ProtocalA | 30 mA | 20 kv | .0 | 3 |

At block 203, an optimal group may be selected from the target group, and each of the reference information samples in the optimal group has a reconstructed image quality higher than a first preset score.

Wherein, the first preset score may be set by the user, and can indicate that the reconstructed image quality is suitable for clinical diagnosis. For example, when the above 5 point scoring system is used to score the reconstructed image quality, the first pre-set score may be set as 3 point score and indicate that a few of artefact and noise can be found in the reconstructed image but the reconstructed image can still be used for disease diagnosis. In this way, since the reconstructed image quality of each of the reference information samples in the target group as illustrated in Table is equal to or higher than 3 point score, the whole target group is taken as an optimal group.

At block 204, a scanning parameter optimization may be performed according to reconstructed image qualities and scanning parameter values of reference information samples in the optimal group, so as to acquire a target scanning parameter value corresponding to the subject information and the scanning protocol of the target group.

Generally, a scanning parameter may be optimized according to any one or more of the following principles:

Principle A, for an axial scan, the X-ray irradiation dose may be viewed as a product of the tube current and the scanning time (mAs=mA*s), and may be lowered by decreasing the tube current and/or the scanning time.

Principle B, for a spiral scan, the X-ray irradiation dose may be viewed as a value acquired by dividing a product of the tube current and the scanning time with the pitch (mAs=mA*s/pitch), and may be lowered by decreasing the tube current, decreasing the scanning time and/or increasing the pitch.

Principle C, for a reconstructed image with obvious noise, the X-ray irradiation dose may remain unchanged by increasing the tube current while adjusting the pitch.

Principle D, for a reconstructed image having artefact, the pitch or collimation parameter may be adjusted. For example, for a reconstructed image with windmill artefact, the pitch may be decreased, or a procedure of scanning with thin slice while reconstructing with thick slice may be adopted. Wherein, the procedure of scanning with thin slice while reconstructing with thick slice may indicate scanning a subject with a thin slice (such as a slice of a thickness smaller than 5 mm) to collect raw data and reconstructing with a thick slice (such as a slice of a thickness larger than 5 mm) to acquire a CT image.

Principle E, in a case that the above 5 point scoring system is used to score the reconstructed image quality, when performing the scanning parameter optimization, average of the scanning parameter values may be calculated from the reference information samples having a reconstructed image quality of 3 point score in the optimal group and taken as a target scanning parameter value of the target group. In this way, by adjusting the scanning parameter values of the reference information samples having a reconstructed image quality of 4 or 5 point score in the target group, the X-ray irradiation dose may be lowered.

Principle F, in a case that the above 5 point scoring system is used to score the reconstructed image quality, average of X-ray irradiation dose may be calculated from the reference information samples having a reconstructed image quality of 3, 4 and 5 point scores in the optimal group and taken as the optimal X-ray irradiation dose of the target group. In this way, compared with the Principle E, the reconstructed image quality may be improved.

Principle G, in a case that the pitch is to be decreased for improving quality of a reconstructed image with windmill artefact, the X-ray irradiation dose may remain unchanged or be lowered by decreasing the tube current properly.

It can be known from the above that, the target scanning parameter value may be set as average of the scanning parameter values for the reference information samples in the optimal group, or the scanning parameter value of one reference information sample in the optimal group, even or may be acquired in any other ways.

For example, for the target group illustrated in the Table 1, when the whole target group is viewed as an optimal group as above, the scanning parameter may be optimized according to the Principle E. Such as, for each of the reference information samples having a reconstructed image quality of 3 point score in the optimal group, average of the tube current is 125 mA, average of the tube voltage is 120 kv and average of the pitch is 1.9, and these average values may be set as corresponding target scanning parameter values.

At block 205, a reference X-ray irradiation dose corresponding to the scanning protocol and the subject information of the target group may be determined according to the target scanning parameter value.

According to an example, the reference X-ray irradiation dose may be calculated according to the following equation:

$$mAs_{scan} = DoesRightFactor^2 * mAs_{ref} * pow\left(\frac{\exp(-\mu_{water}*D_{ref})}{\exp(-\mu_{water}*D_{scan})}, adjCoef\right); \quad (4)$$

wherein, $\text{mAs}_{scan}$ represents a reference X-ray irradiation dose corresponding to the target scanning parameter value, $\text{mAs}_{ref}$ represents a default optimal X-ray irradiation dose of the scanning protocol, DoesRightFactor represents a regulatory factor and may be 1 or changed according to specific scanning protocol, $\mu_{water}$ represents an attenuation coefficient of water, $D_{ref}$ represents a default attenuation diameter of equivalent water phantom in the scanning protocol, $D_{scan}$ represents an attenuation diameter of equivalent water phantom of the examined subject, adjCoef represents an adjusting coefficient and may be 0.5 or changed according to specific scanning protocol.

The calculated reference X-ray irradiation dose may be viewed as optimal X-ray irradiation dose corresponding to the scanning protocol and the subject information of the target group, and the scanning protocol may be modified according to the reference X-ray irradiation dose. Then, when performing a CT scanning according to the modified scanning protocol, an optimal X-ray irradiation dose suitable for a specific to-be-scanned region of a subject having specific body size may be calculated according to the equation (4), and thus subjects of different body sizes may be scanned with corresponding optimal X-ray irradiation dose.

For example, for a target group illustrated in the Table 1, when the determined target scanning parameter values include tube current of 125 mA, tube voltage of 120 kv and pitch of 1.9, according to a default optimal X-ray irradiation dose of the protocol ProtocalA which corresponds to the equivalent diameter of 400 mm and the target scanning parameter values, an optimized reference X-ray irradiation dose NewmAs of the protocol ProtocalA may be calculated according to the equation (4). Then, the optimized reference X-ray irradiation dose NewmAs may be used to modify the protocol ProtocalA, and after this, a subject may be scanned according to the modified protocol ProtocalA.

According to an example, after a reconstructed image is acquired by scanning a subject according to the modified scanning protocol, it may determine whether quality of the reconstructed image is lower than a first preset score, such as not suitable for disease diagnosis, and when the determination result is YES, blocks 201-205 may be repeated to perform a scanning parameter optimization again. In this way, accuracy of the target scanning parameter value may be improved.

Figure 3:
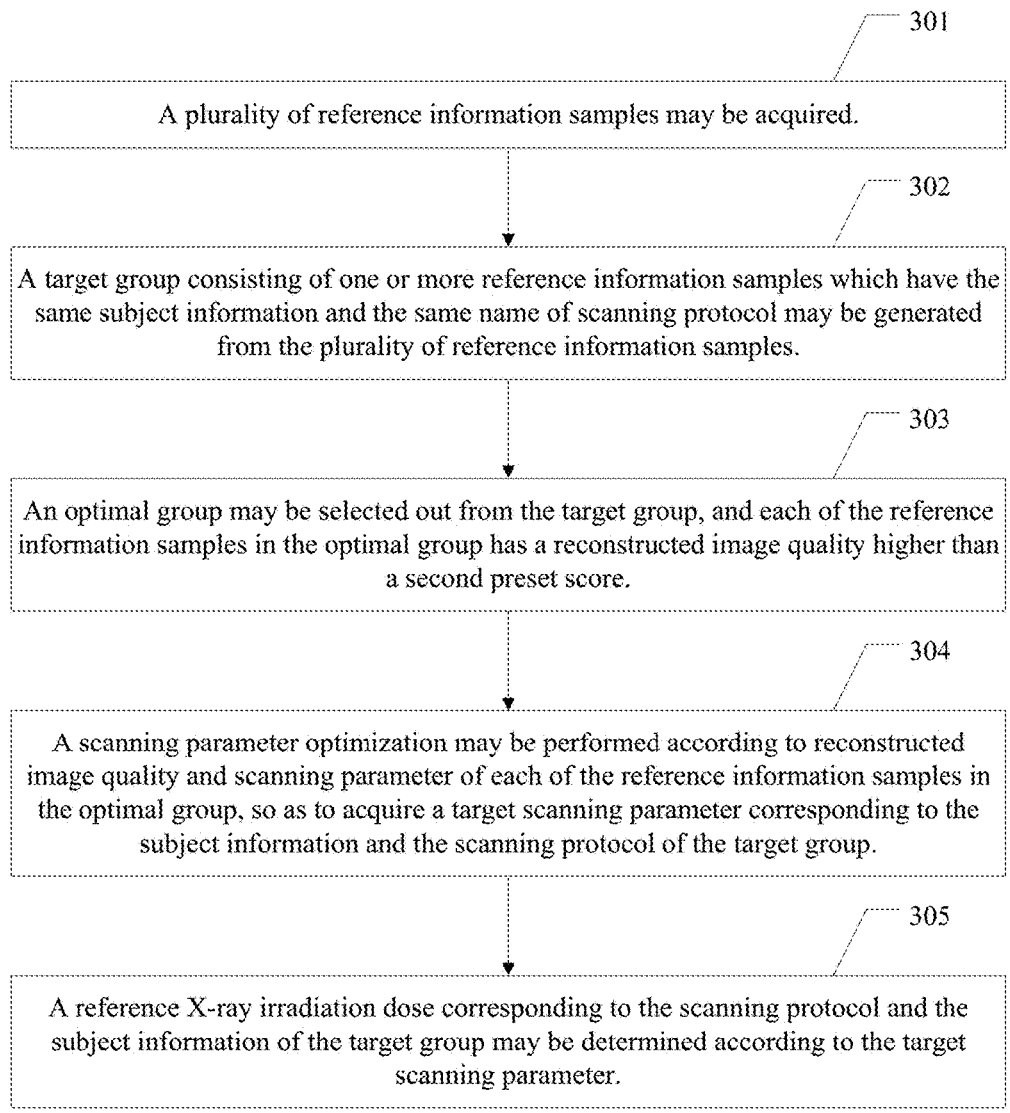
FIG. 3 is a flowchart illustrating a method for optimizing CT scanning parameter according to still another example of the present disclosure.

FIG. 3 illustrates a method for optimizing CT scanning parameter according to another example of the present disclosure, and the method may include blocks 301-305.

At block 301, a plurality of reference information samples may be acquired, wherein each of the reference information samples may include subject information, information indicating a scanning protocol, one or more scanning parameter values and information indicating reconstructed image quality obtained accordingly.

It should be understood that, the scanning protocol may indicate a region which is scanned or to-be-scanned. The subject information may include one or more selected from the following: body size, gender, age and body mass index. The scanning parameters may include one or more selected from the following: tube current, tube voltage, scanning time, scanning slice thickness, pitch and scanning volume. The reconstructed image quality may include a score indicating an evaluation on quality of the reconstructed image, such as a score indicating overall quality, a score indicating noise level, a score indicating artefact level, a score indicating windmill artefact level or a score indicating cone-beam artefact level.

According to an example, the subject information may be an X-ray attenuation diameter of equivalent water phantom, and the X-ray attenuation diameter of equivalent water phantom may be calculated according to pilot film data or projection data as described above.

According to another example, the subject information may be an equivalent diameter, and the equivalent diameter may be calculated according to a reconstructed image as described above.

Besides the above examples, one skilled in the art would understand that, the subject information may be determined in any other ways.

At block 302, a target group consisting of one or more reference information samples with the same subject information and the same scanning protocol may be generated from the plurality of reference information samples.

For example, a generated target group may be as illustrated in the Table 1.

At block 303, an optimal group may be selected from the target group, and each of the reference information samples in the optimal group has a reconstructed image quality higher than a second preset score.

Wherein, the second preset score may be set by the user, and can indicate a reconstructed image quality higher than that indicated by the first preset score, such as the reconstructed image without artefact and noise. For example, when the above 5 point scoring system is used to score the reconstructed image quality, the second preset score may be set as 4 or 5 point score. In this way, for the target group illustrated in the Table 1, since only one reference information sample has a reconstructed image quality equal to or higher than 4 point score, the whole optimal group includes only one reference information sample.

At block 304, a scanning parameter optimization may be performed according to reconstructed image qualities and scanning parameter values of reference information samples in the optimal group, so as to acquire a target scanning parameter value corresponding to the subject information and the scanning protocol of the target group.

As described above, a target scanning parameter value may be set as average of scanning parameter values for the reference information samples in the optimal group, or a scanning parameter value of one reference information sample in the optimal group, even or be acquired in any other ways.

For example, for the target group as illustrated in the Table 1, when the optimal group includes only one reference information sample, the scanning parameter optimization may be performed according to above Principle E or F. Such as, for the only one reference information sample having a reconstructed image quality of 4 point score in the optimal group, the tube current is 150 mA, the tube voltage is 120 kv and the pitch is 1.7, and these scanning parameter values may be set as corresponding target scanning parameter values.

At block 305, a reference X-ray irradiation dose corresponding to the scanning protocol and the subject information of the target group may be determined according to the target scanning parameter values.

For example, the reference X-ray irradiation dose may be calculated according to the above equation (4).

The calculated reference X-ray irradiation dose may be viewed as optimal X-ray irradiation dose corresponding to the scanning protocol and the subject information of the target group, and the scanning protocol may be modified according to the reference X-ray irradiation dose. Then, when performing a CT scanning according to the modified scanning protocol, an optimal X-ray irradiation dose suitable for a specific to-be-scanned region of a subject having specific body size may be calculated according to the equation (4), and thus subjects of different body sizes may be scanned with corresponding optimal X-ray irradiation dose.

According to an example, after a reconstructed image is acquired by scanning a subject according to the modified scanning protocol, it may determine whether quality of the reconstructed image is not suitable for disease diagnosis, and when the determination result is YES, blocks 301-305 may be repeated to perform a scanning parameter optimization again. In this way, accuracy of the target scanning parameter value may be improved.

Figure 4:
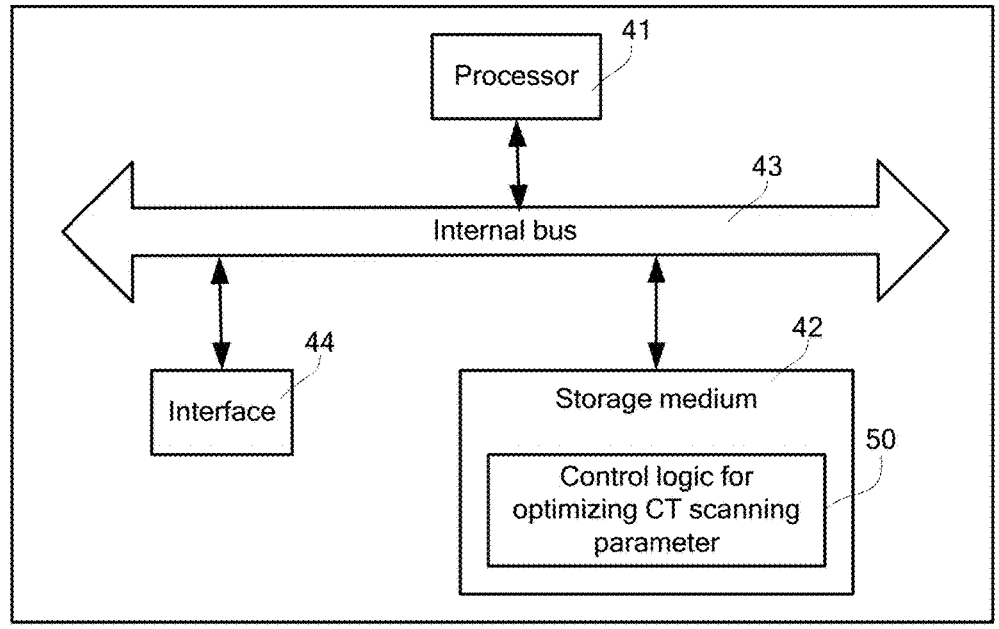
FIG. 4 schematically illustrates a hardware structure of a device for optimizing CT scanning parameter according to an example of the present disclosure.

The present disclosure also provides a device for optimizing CT scanning parameter. Referring to FIG. 4, the device may include a processor 41 and machine readable storage medium 42, wherein, the processor 41 and the machine readable storage medium 42 are connected with each other through an internal bus 43. In other possible implementations, the device may further include an interface 44 so as to communicate with other external devices or components.

In different examples, the machine readable storage medium 42 may be random access memory (RAM), transitory memory, non-transitory memory, flash memory, storage drive (such as hard disk drive), solid state hard disk, other types of storage disks (such as optical disk and DVD, etc), or similar types of storage medium, or combinations thereof.

Figure 5:
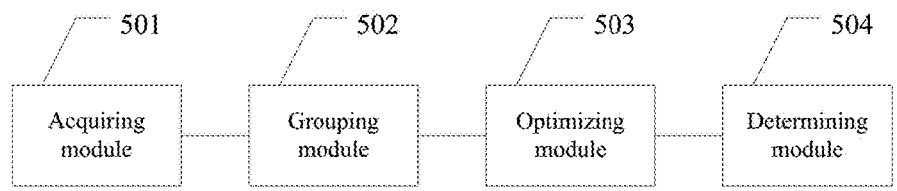
FIG. 5 is a block diagram illustrating functional modules of a control logic for optimizing CT scanning parameter according to an example of the present disclosure.

Further, the machine readable storage medium 42 may be stored with control logic 50 for optimizing CT scanning parameter. In terms of functionality, as illustrated in FIG. 5, the control logic 50 may comprise:

an acquiring module 501, configured to acquire a plurality of reference information samples, wherein, each of the reference information samples may include subject information, information indicating a scanning protocol, one or more scanning parameter values and information indicating reconstructed image quality (such as a score indicating evaluation on quality of the reconstructed image obtained accordingly);

a grouping module 502, configured to, from the reference information samples acquired by the acquiring module 501, generate a target group consisting of one or more reference information samples which have the same subject information and the same scanning protocol;

an optimizing module 503, configured to, according to reconstructed image qualities and scanning parameter values of reference information samples in the target group generated by the grouping module 502, perform a scanning parameter optimization to acquire a target scanning parameter value corresponding to the subject information and the scanning protocol of the target group; and a determining module 504, configured to, according to the target scanning parameter value acquired by the optimizing module 503, determine a reference X-ray irradiation dose corresponding to the scanning protocol and the subject information of the target group.

Wherein, the calculated reference X-ray irradiation dose may be viewed as optimal X-ray irradiation dose corresponding to the scanning protocol and the subject information of the target group, and the scanning protocol may be modified according to the reference X-ray irradiation dose. Then, when performing a CT scanning according to the modified scanning protocol, an optimal X-ray irradiation dose suitable for a specific to-be-scanned region of a subject having specific body size may be calculated according to the equation (4), and thus subjects of different body sizes may be scanned with corresponding optimal X-ray irradiation dose.

Figure 6:
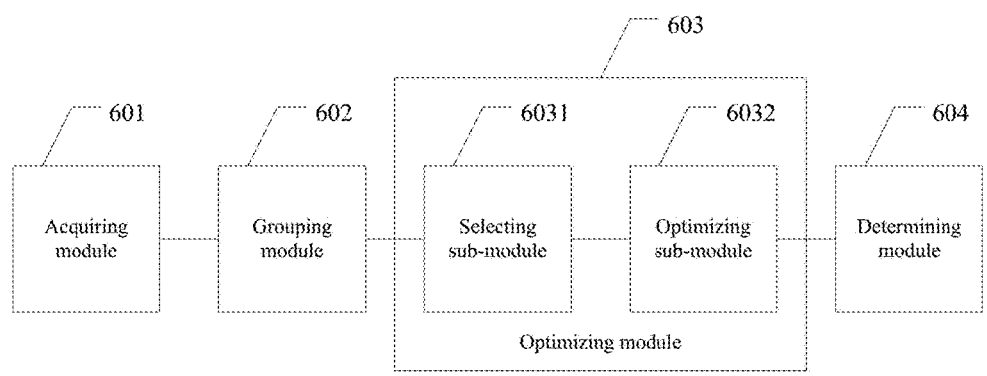
FIG. 6 is a block diagram illustrating functional modules of a control logic for optimizing CT scanning parameter according to another example of the present disclosure.

According to another example, as illustrated in FIG. 6, the control logic 50 may include:

an acquiring module 601, configured to acquire a plurality of reference information samples, and each of the plurality of reference information samples may include subject information, information indicating a scanning protocol, one or more scanning parameter values and information indicating reconstructed image quality (such as a score indicating evaluation on quality of the reconstructed image obtained accordingly), wherein, the scanning protocol may indicate a region which is scanned or to-be-scanned; the subject information may include one or more selected from the following: body size, gender, age and body mass index; the scanning parameters may include one or more of the following: tube current, tube voltage, scanning time, scanning slice thickness, pitch and scanning volume; the reconstructed image quality may include a score indicating overall quality, a score indicating noise level, a score indicating artefact level, a score indicating windmill artefact level or a score indicating cone-beam artefact level;

a grouping module 602, configured to, from the reference information samples acquired by the acquiring module 601, generate a target group consisting of one or more reference information samples which have the same subject information and the same scanning protocol;

an optimizing module 603, configured to, according to reconstructed image qualities and scanning parameter values of reference information samples in the target group generated by the grouping module 602, perform a scanning parameter optimization to acquire a target scanning parameter value corresponding to the subject information and the scanning protocol of the target group;

a determining module 604, configured to, according to the target scanning parameter value acquired by the optimizing module 603, determine a reference X-ray irradiation dose corresponding to the scanning protocol and the subject information of the target group.

According to an example, the optimizing module 603 may include:

a selecting sub-module 6031, configured to select an optimal group from the target group and each of the reference information samples in the optimal group has a reconstructed image quality higher than a preset score; wherein, the preset score may indicate that reconstructed image quality is suitable for clinical diagnosis; and an optimizing sub-module 6032, configured to, according to reconstructed image qualities and scanning parameter values of reference information samples in the optimal group, perform a scanning parameter optimization to acquire a target scanning parameter value corresponding to the subject information and the scanning protocol of the target group.

A software implementation will be described below as an example to further illustrate how the device for optimizing CT scanning parameter operates control logic 50. In this example, the control logic 50 of the present disclosure should be understood as machine executable instructions stored in the machine readable storage medium 42. When the processor 41 on the device of the present disclosure executes the control logic 50, by revoking the instructions of functional modules corresponding to the control logic 50 stored in the machine readable storage medium 42, the processor 41 performs the following operations:

acquiring a plurality of reference information samples, wherein each of the reference information samples includes subject information, information indicating a scanning protocol, one or more scanning parameter values and information indicating reconstructed image quality;

generating a target group from the plurality of reference information samples, wherein the target group consists of one or more reference information samples which have the same subject information and the same scanning protocol;

performing a scanning parameter optimization according to reconstructed image qualities and scanning parameter values of reference information samples in the target group, so as to acquire a target scanning parameter value corresponding to the subject information and the scanning protocol of the target group; and determining a reference X-ray irradiation dose according to the target scanning parameter value, wherein the reference X-ray irradiation dose corresponds to the scanning protocol and the subject information of the target group.

According to an example, when performing the scanning parameter optimization, the machine executable instructions may further cause the processor to perform the following operations:

selecting out an optimal group from the target group, wherein each of the reference information samples in the optimal group has a reconstructed image quality higher than a first preset score; and performing a scanning parameter optimization according to reconstructed image qualities and scanning parameter values of reference information samples in the optimal group.

According to an example, the machine executable instructions may further cause the processor to determine the subject information of a reference information samples by:

converting pilot film data of a slice corresponding to the reference information sample or projection data of a field view image in the reference information sample into an equivalent attenuation domain;

calculating an equivalent attenuation area according to the data in the equivalent attenuation domain;

calculating an attenuation diameter of equivalent water phantom according to the equivalent attenuation area; and taking the attenuation diameter of equivalent water phantom as the subject information of the reference information sample.

Further, the machine executable instructions may further cause the processor to calculate the equivalent attenuation area S as follows:

$$S = \sum_{i=0}^{N-1} (\mu_i l_i + \mu_{i+1} l_{i+1}) * \Delta / 2;$$

the N represents the number of detecting channels in a CT scanner system, the $\mu_i$ represents an average attenuation coefficient corresponding to the $i^{th}$ detecting channel, the $l_i$ represents a length of attenuation path corresponding to the $i^{th}$ detecting channel, and the $\Delta$ represents a distance between centers of two adjacent detecting units.

Further, the machine executable instructions may further cause the processor to calculate the diameter $D_{scan}$ of equivalent water phantom as follows:

$$D_{scan} = 2*\text{sqrt}(\text{mean}(S)/\pi)/\mu_{water};$$

wherein, the $\mu_{water}$ represents an attenuation coefficient of water, and the $\pi$ represents the circumference ratio.

According to another example, the machine executable instructions may further cause the processor to determine the subject information of a reference information samples by:

determining the major axis and the minor axis of a reconstructed image corresponding to the reference information sample;

simulating an equivalent ellipse according to the major axis and the minor axis;

converting the equivalent ellipse into an equivalent circular of the same area;

calculating the diameter of the equivalent circular as an equivalent diameter; and taking the equivalent diameter as the subject information of the reference information sample.

According to an example, when determining a reference X-ray irradiation dose corresponding to the scanning protocol and the subject information, the machine executable instructions may further cause the processor to calculate the reference X-ray irradiation dose as follows:

$$mAs_{scan} = DoesRightFactor^2 * mAs_{ref} * pow\left(\frac{\exp(-\mu_{water} * D_{ref})}{\exp(-\mu_{water} * D_{scan})}, adjCoef\right);$$

wherein, the $mAs_{scan}$ represents the reference X-ray irradiation dose corresponding to the target scanning parameter value, the $mAs_{ref}$ represents a default optimal X-ray irradiation dose of the scanning protocol, the DoesRightFactor represents a regulatory factor, the $\mu_{water}$ represents an attenuation coefficient of water, the $D_{ref}$ represents a default attenuation diameter of equivalent water phantom in the scanning protocol, the $D_{scan}$ represents an attenuation diameter of equivalent water phantom of examined subject, and the adjCoef represents an adjusting coefficient.

The above are only preferred examples of the present disclosure is not intended to limit the disclosure within the spirit and principles of the present disclosure, any changes made, equivalent replacement, or improvement in the protection of the present disclosure should contain within the range.

The methods, processes and units described herein may be implemented by hardware (including hardware logic circuitry), software or firmware or a combination thereof. The term 'processor' is to be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

Further, the processes, methods and functional units described in this disclosure may be implemented in the form of a computer software product. The computer software product is stored in a storage medium and comprises a plurality of instructions for making a processor to implement the methods recited in the examples of the present disclosure.

The figures are only illustrations of an example, wherein the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for optimizing a CT scanning parameter, includes:

acquiring a plurality of reference information samples, wherein each of the reference information samples includes subject information, information indicating a scanning protocol, one or more scanning parameter values and information indicating reconstructed image quality, wherein the subject information of the reference information sample comprises one or more from a body size, a gender, an age and a body mass index, and the scanning protocol of the reference information sample indicates a region which is scanned based on the one or more scanning parameter values;

generating a target group from the plurality of reference information samples, wherein the target group consists of one or more reference information samples in which the subject information is same as that of a subject to be scanned and the scanning protocol indicates a region to be scanned of the subject;

selecting an optimal group from the target group, wherein each of the reference information samples in the optimal group has a reconstructed image quality higher than a first preset score;

obtaining an average of scanning parameter values of reference information samples in the optimal group as a target scanning parameter value;

determining a reference X-ray irradiation dose according to the target scanning parameter value, wherein the reference X-ray irradiation dose corresponds to the scanning protocol and the subject information of the target group; and obtaining a reconstructed image of the region of the subject by scanning the region of the subject based on the target scanning parameter value and the reference X-ray irradiation dose;

wherein the subject information of a reference information sample is determined by:
converting pilot film data of a slice corresponding to the reference information sample or projection data of a field view image in the reference information sample into an equivalent attenuation domain;
calculating an equivalent attenuation area according to the data in the equivalent attenuation domain;
calculating an attenuation diameter of an equivalent water phantom according to the equivalent attenuation area; and
taking the attenuation diameter of the equivalent water phantom as the subject information of the reference information sample;

wherein the equivalent attenuation area is calculated as follows:

$$S = \sum_{i=0}^{N-1} (\mu_i l_i + \mu_{i+1} l_{i+1}) * \Delta / 2;$$

wherein, the S represents the equivalent attenuation area,
the N represents the number of detecting channels in a CT scanner system, wherein the CT scanner system comprises a detector with multiple, adjacent detecting units,
the $\mu_i$ represents an average attenuation coefficient corresponding to the $i^{th}$ detecting channel,
the $l_i$ represents a length of attenuation path corresponding to the $i^{th}$ detecting channel, and
the $\Delta$ represents a distance between centers of two adjacent detecting units in the CT scanner system.

2. The method of claim 1, wherein the attenuation diameter of the equivalent water phantom is calculated as follows:

$$D_{scan} 2*\text{sqrt}(\text{mean}(S)/\pi/\mu_{water});$$

wherein, the $D_{scan}$ represents the attenuation diameter of the equivalent water phantom,
the $\mu_{water}$ represents an attenuation coefficient of water, and
the $\pi$ represents a circumference ratio.

3. A method for optimizing a CT scanning parameter, includes:

acquiring a plurality of reference information samples, wherein each of the reference information samples includes subject information, information indicating a scanning protocol, one or more scanning parameter values and information indicating reconstructed image quality, wherein the subject information of the reference information sample comprises one or more from a body size, a gender, an age and a body mass index, and the scanning protocol of the reference information sample indicates a region which is scanned based on the one or more scanning parameter values;

generating a target group from the plurality of reference information samples, wherein the target group consists of one or more reference information samples in which the subject information is same as that of a subject to be scanned and the scanning protocol indicates a region to be scanned of the subject;

selecting an optimal group from the target group, wherein each of the reference information samples in the optimal group has a reconstructed image quality higher than a first preset score;

obtaining an average of scanning parameter values of reference information samples in the optimal group as a target scanning parameter value;

determining a reference X-ray irradiation dose according to the target scanning parameter value, wherein the reference X-ray irradiation dose corresponds to the scanning protocol and the subject information of the target group; and obtaining a reconstructed image of the region of the subject by scanning the region of the subject based on the target scanning parameter value and the reference X-ray irradiation dose;

wherein, wherein the subject information of a reference information sample is determined by:

determining a major axis and a minor axis of a reconstructed image corresponding to the reference information sample;

simulating an equivalent ellipse according to the major axis and the minor axis;

converting the equivalent ellipse into an equivalent circle of the same area;

calculating the diameter of the equivalent circle as an equivalent diameter; and taking the equivalent diameter as the subject information of the reference information sample.

4. A method for optimizing a CT scanning parameter, includes:

acquiring a plurality of reference information samples, wherein each of the reference information samples includes subject information, information indicating a scanning protocol, one or more scanning parameter values and information indicating reconstructed image quality, wherein the subject information of the reference information sample comprises one or more from a body size, a gender, an age and a body mass index, and the scanning protocol of the reference information sample indicates a region which is scanned based on the one or more scanning parameter values;

generating a target group from the plurality of reference information samples, wherein the target group consists of one or more reference information samples in which the subject information is same as that of a subject to be scanned and the scanning protocol indicates a region to be scanned of the subject;

selecting an optimal group from the target group, wherein each of the reference information samples in the optimal group has a reconstructed image quality higher than a first preset score;

performing a scanning parameter optimization according to reconstructed image qualities and scanning parameter values of reference information samples in the optimal group, so as to acquire a target scanning parameter value corresponding to the subject information and the scanning protocol of the target group;

determining a reference X-ray irradiation dose according to the target scanning parameter value, wherein the reference X-ray irradiation dose corresponds to the scanning protocol and the subject information of the target group; and obtaining a reconstructed image of the region of the subject by scanning the region of the subject based on the target scanning parameter value and the reference X-ray irradiation dose;

wherein, the reference X-ray irradiation dose is determined by calculating with the following equation:

$$mAs_{scan} = DoesRightFactor^2 * mAs_{ref} * pow\left(\frac{\exp(-\mu_{water} * D_{ref})}{\exp(-\mu_{water} * D_{scan})}, adjCoef\right);$$

wherein, the $mAs_{scan}$ represents a reference X-ray irradiation dose corresponding to the target scanning parameter value, the $mAs_{ref}$ represents a default optimal X-ray irradiation dose of the scanning protocol, the DoesRightFactor represents a regulatory factor, the $\mu_{water}$ represents an attenuation coefficient of water, the $D_{ref}$ represents a default attenuation diameter of an equivalent water phantom in the scanning protocol, the $D_{scan}$ represents an attenuation diameter of the equivalent water phantom of an examined subject, and the adjCoef represents an adjusting coefficient.

5. The method of claim 1, wherein, the reconstructed image quality of a reference information sample includes any one selected from the following:

a score indicating overall quality of a reconstructed image corresponding to the reference information sample, a score indicating noise level of the reconstructed image, a score indicating artifact level of the reconstructed image, a score indicating windmill artifact level of the reconstructed image, and a score indicating cone-beam artifact level of the reconstructed image.

6. A device for optimizing a CT scanning parameter, including a processor configured to invoke and execute machine executable instructions which correspond to control logic for optimizing the CT scanning parameter and are stored in a storage medium, the machine executable instructions cause the processor to perform the method of claim 1.

7. The device of claim 6, wherein, the machine executable instructions further cause the processor to calculate the attenuation diameter of the equivalent water phantom as follows:

$$D_{scan}=2*\text{sqrt}(\text{mean}(S)/\pi)\mu_{water};$$

wherein, the $D_{scan}$ represents an attenuation diameter of the equivalent water phantom, the $\mu_{water}$ represents an attenuation coefficient of water, and the $\pi$ represents a circumference ratio.

8. A device for optimizing a CT scanning parameter, including a processor configured to invoke and execute machine executable instructions which correspond to control logic for optimizing the CT scanning parameter and are stored in a storage medium, the machine executable instructions cause the processor to perform the method of claim 3.

9. A device for optimizing a CT scanning parameter, including a processor configured to invoke and execute machine executable instructions which correspond to control logic for optimizing the CT scanning parameter and are stored in a storage medium, the machine executable instructions cause the processor to perform the method of claim 4.

10. The device of claim 6, wherein, the reconstructed image quality of a reference information sample includes any one selected from the following:

a score indicating overall quality of a reconstructed image corresponding to the reference information sample, a score indicating noise level of the reconstructed image, a score indicating artifact level of the reconstructed image, a score indicating windmill artifact level of the reconstructed image, and a score indicating cone-beam artifact level of the reconstructed image.

* * * * *